(12) United States Patent
Hirsch et al.

(10) Patent No.: US 7,074,613 B1
(45) Date of Patent: Jul. 11, 2006

(54) MONOCLONAL ANTIBODY DIRECTED AGAINST CELLS OF HUMAN RENAL CELL CARCINOMA

(75) Inventors: François Hirsch, Arcueil (FR); Eric Angevin, Villevoques (FR)

(73) Assignee: Centre National de la Rechershe Scientifique, Paris (FR)

( * ) Notice: Subject to any disclaimer, the term of this patent is extended or adjusted under 35 U.S.C. 154(b) by 0 days.

(21) Appl. No.: 09/959,911

(22) PCT Filed: May 10, 2000

(86) PCT No.: PCT/FR00/01258

§ 371 (c)(1),
(2), (4) Date: Feb. 1, 2002

(87) PCT Pub. No.: WO00/67792

PCT Pub. Date: Nov. 16, 2000

(30) Foreign Application Priority Data

May 10, 1999 (FR) .................................. 99 05942

(51) Int. Cl.
*C12N 5/16* (2006.01)
*C12Q 1/70* (2006.01)
*C07K 16/00* (2006.01)
*C12P 21/08* (2006.01)

(52) U.S. Cl. .......................... 435/326; 435/5; 435/328; 435/330; 530/387.1; 530/387.3; 530/388.1; 530/391.3

(58) Field of Classification Search ..... 424/178.1–183; 435/326–345; 530/387.1–391
See application file for complete search history.

(56) References Cited

U.S. PATENT DOCUMENTS

| | | | | |
|---|---|---|---|---|
| 5,270,202 A | * | 12/1993 | Raychaudhuri | ............. 435/327 |
| 6,235,280 B1 | * | 5/2001 | Chatterjee et al. | ....... 424/131.1 |
| 6,632,431 B1 | * | 10/2003 | Wu | ......................... 424/131.1 |

FOREIGN PATENT DOCUMENTS

| | | |
|---|---|---|
| FR | EP 0 160 250 | 11/1985 |
| FR | EP 0 210 970 | 2/1987 |
| FR | EP 0 119 528 | 5/1992 |
| WO | WO 88 08854 | 11/1988 |
| WO | WO 90/14595 | 11/1990 |
| WO | WO 00/67792 | 11/2000 |

OTHER PUBLICATIONS

Weiner L.M., (Seminars Oncology, vol. 26, No. 4, Suppl 12, pp. 41-50, 1999).*
Gura (Science, v278, 1997, pp. 1041-1042).*
Orkin and Motulsky (NIH ad hoc committee Dec. 1995—http://www.nih.gov/news/panelrep.html).*
Theodore Friedmann (scientific American Jun. 1997, pp. 96-101).*
Inder Verma et al (Nature Sep. 1997; 389:239-242).*
Rubanyi GM (Molecular Aspects of Medecine 2001;22:113-142).*
International Search Report, Sep. 8, 2000.

* cited by examiner

*Primary Examiner*—Christopher Yaen
(74) *Attorney, Agent, or Firm*—Finnegan, Henderson, Farabow, Garrett & Dunner LLP (57) ABSTRACT

The invention concerns a hybridome called 5C5 (CNCM no I-2184) and the monoclonal antibody 5C5 which it produces. Said monoclonal antibody which specifically recognises most human renal cell carcinomas, is developed for diagnosing, imaging and treating human renal cell carcinomas.

31 Claims, 8 Drawing Sheets

RCC TYPAGE

PIUZ RCC

| Label | Events | % Sorted | % Total | Mean |
|---|---|---|---|---|
| All | 5767 | 100.00 | 78.18 | 4.02 |
| M1 | 37 | 0.64 | 0.50 | 17.70 |

| Label | Events | % Sorted | % Total | Mean |
|---|---|---|---|---|
| All | 5832 | 100.00 | 75.65 | 24.13 |
| M1 | 3543 | 60.75 | 45.96 | 33.97 |

| Label | Events | % Sorted | % Total | Mean |
|---|---|---|---|---|
| All | 5829 | 100.00 | 78.59 | 10.52 |
| M1 | 870 | 14.93 | 11.73 | 38.21 |

FIG_1A...

RCC TYPAGE

LAWR RCC

| Label | Events | % Sorted | % Total | Mean |
|---|---|---|---|---|
| All | 5447 | 100.00 | 89.59 | 3.13 |
| M1 | 5 | 0.09 | 0.08 | 16.09 |

| Label | Events | % Sorted | % Total | Mean |
|---|---|---|---|---|
| All | 5350 | 100.00 | 90.02 | 17.06 |
| M1 | 2377 | 44.43 | 40.00 | 28.03 |

| Label | Events | % Sorted | % Total | Mean |
|---|---|---|---|---|
| All | 5293 | 100.00 | 91.48 | 3.16 |
| M1 | 39 | 0.74 | 0.67 | 43.53 |

FIG_1A

RCC TYPAGE

DOBS RCC

| Label | Events | % Sorted | % Total | Mean |
|---|---|---|---|---|
| All | 5363 | 100.00 | 55.68 | 4.12 |
| M1 | 37 | 0.69 | 0.38 | 16.64 |

| Label | Events | % Sorted | % Total | Mean |
|---|---|---|---|---|
| All | 4908 | 100.00 | 49.39 | 22.31 |
| M1 | 2644 | 53.87 | 26.61 | 34.74 |

| Label | Events | % Sorted | % Total | Mean |
|---|---|---|---|---|
| All | 5207 | 100.00 | 51.60 | 14.60 |
| M1 | 1912 | 36.72 | 18.95 | 25.47 |

FIG_1B

RCC TYPAGE

GUIL RCC

| Label | Events | % Sorted | % Total | Mean |
|---|---|---|---|---|
| All | 5088 | 100.00 | 73.53 | 3.64 |
| M1 | 32 | 0.63 | 0.46 | 18.46 |

| Label | Events | % Sorted | % Total | Mean |
|---|---|---|---|---|
| All | 5079 | 100.00 | 71.90 | 16.02 |
| M1 | 2525 | 49.71 | 35.74 | 23.29 |

| Label | Events | % Sorted | % Total | Mean |
|---|---|---|---|---|
| All | 5085 | 100.00 | 74.01 | 22.66 |
| M1 | 2971 | 58.43 | 43.24 | 33.40 |

FIG_1B

MONOCLONAL ANTIBODY DIRECTED AGAINST CELLS OF HUMAN RENAL CELL CARCINOMA

This application is based on and claims the benefit of French application 99/05,942, filed May 10, 1999, and International application PCT/FR00/01258, filed May 10, 2000. The entire disclosure of these applications are relied upon and incorporated by reference herein.

The present invention relates to a novel hybridoma which produces a monoclonal antibody directed specifically against a human renal cell carcinoma (RCC) antigen; the invention also relates to the use of this monoclonal antibody, in particular for diagnosing, imaging and treating RCCs.

RCCs are cancers which are particularly difficult to diagnose in disseminated forms (Oberling et al. (1960) Nature 186, 402–403; Holthafer et al. (1983) Lab. Invest. 49, 319–326), and which represent each year approximately 5% of new cancer cases. Besides first line surgery, there is, at the current time, no effective treatment in the event of recurrence.

A monoclonal antibody (mAb) specific for an antigen present in a predominant manner only on human renal carcinoma cells would be extremely useful for diagnosing, localizing and treating this disease. A limited number of mAbs directed against human RCCs have been reported in the literature (Oosterwijk E et al. (1986) Int. J. Cancer 38: 489–494; Kinouchi T. et al. (1995) J. Urol. 154: 288–292; Kaufmann O. et al. (1997) Histopathology 31:31–37) or have been the subject of patents or patent applications (EP 119 528, EP 160 250, EP 210 970, WO 88/08854, Wo 90/14595).

Among the antibodies currently available, none has the qualities required for diagnosis, imaging and/or therapy. Thus, for example, the G250 antibody (WO 88/08854, inventors Oosterwijk E. and Warnaar S. O.), the most studied and the most used of the mAbs directed against RCCs, since used in two clinical studies of immunoradiolocalization of primary tumors or metastases (Oosterwijk E. et al. (1993) J. Clin. Oncol. 11: 738–750; Steffens M. G. et al. (1997) J. Clin. Oncol. 15: 1529–1537), recognizes only 70 to 80% of tumors. However, to date, no therapeutic effect has been obtained with the G250 antibody. Another limit to exploiting this antibody lies in the fact that human tumors expressing the G250 antigen can develop only with great difficulty in mice, making it difficult to produce a good animal model for targeting in vivo, via the G250 mAb.

These results therefore emphasize the need to obtain other monoclonal antibodies, which are specific for a different antigen and which recognize RCCs in a highly specific manner without having substantial reactivity with normal cells.

The inventors have used the hybridoma technique initially developed by Köhler and Milstein (Nature (1975) 256: 495–497) to obtain a novel hybridoma that produces a novel monoclonal antibody that is highly specific for human renal carcinomas and recognizes a specific antigen other than the G250 antigen. A subject of the present invention is therefore a hybridoma denoted 5C5, as deposited on Apr. 6, 1999 at the CNCM (Collection Nationale de Cultures de Microorganisms, Institut Pasteur, 28, rue de Dr. Roux, 75724 Paris Cedex 15) under the number I-2184, formed by fusing cells of a Balb/C murine myeloma line Sp20 and cells from inquinal and abdominal lymph nodes of a Balb/C mouse having been immunized beforehand with the BIZ human renal carcinoma line.

The present invention therefore relates to a monoclonal antibody specific for most human renal carcinoma cells, named 5C5, which does not bind to the G250 antigen and which can be obtained with the hybridoma of the invention. The monoclonal antibody thus produced was isolated and then characterized. The subclass and the isotype of the monoclonal antibody were determined by the Ouchterlony immunoprecipitation technique which uses rabbit antibodies directed against mouse immunoglobulin subclasses.

The characterization of the 5C5 monoclonal antibody of the present invention was carried out on RCC cell lines and also on tissue fragments from patients suffering from RCC. The analysis of the presence of the renal carcinoma cell antigen specifically recognized by the antibody of the present invention may be carried out by immunohistochemical techniques using, for example, peroxidase staining or by immunofluorescence techniques. According to a standard protocol, the slides on which the frozen sections, obtained on a cryostat, of the unfixed biopsy samples are placed are air-dried and then incubated with the 5C5 monoclonal antibody in a humid chamber at room temperature. The slides are then covered with a preparation of antibody directed against the antibody or the antibody fragment of the present invention. For example, if the 5C5 monoclonal antibody is used, the second antibody may be an anti-mouse antibody. The second antibody may be labeled with a fluorescent compound (fluorescein, Texas-red, DAPI). The nature of the labeling of the sample and also its intensity are then determined using a fluorescence microscope. In immunofluorescence experiments, the antibody according to the invention is characterized in that said antibody or antibody fragment binds specifically to an antigen which is common to the cells of human renal carcinoma lines BIZ, HIEG, QUIE, BENA, PIUZ, GUIL, GUER, ROB, DURI, JOUS, GUIS, LEFR, MEGR, BLAN, DOBS, MOG; the 5C5 monoclonal antibody does not bind to an antigen of cells of the human renal carcinoma line LAWR and does not bind to the G250 antigen.

The high specificity of reaction of the 5C5 antibody was demonstrated by the absence of reactivity of the antibody on cells of human tumor lines other than the RCC cell lines. Thus, the 5C5 monoclonal antibody does not bind to an antigen of cells of human colon tumor lines: HRT18, HTL8R, LS174T, SW48 and SW620, does not bind to an antigen of cells of the human lung tumor line: LX2, does not bind to an antigen of cells of the human stomach tumor line: Kato, does not bind to an antigen of cells of human breast tumor lines: McF7 and ZR75, and does not bind to an antigen of cells of the human ovarian tumor line: OVCAR. With regard to the reactivity of the antibody on normal cells, immunohistochemical experiments have revealed 5C5 monoclonal antibody labeling in the cytoplasm of proximal renal tubes and also the apical pole and lateral faces of colon epithelial cells originating from normal human tissue fragments.

The present invention also relates to the single-chain antibody produced from the monoclonal antibody according to the invention, the chimeric antibody produced from the monoclonal antibody according to the invention and also the humanized antibody produced from the monoclonal antibody according to the invention.

The antibody or the antibody fragment directed against the human renal cell carcinoma antigen can be administered in order to cause an anti-idiotypic or anti-anti-idiotypic immune response. An anti-idiotypic antibody directed against the antibody which reacts against a human renal cell carcinoma antigen may, in fact, express epitopes similar to those of the antigen and may thus be used similarly for immunization and thus for developing an anticancer immune response. An anti-anti-idiotypic antibody may be used in ways similar to those described for the antitumor primary antibody of the present invention. Consequently, it is also within the extent of the invention to use an anti-idiotypic antibody, characterized in that it is directed against the antibody according to the invention, and to use an anti-anti-idiotypic antibody, characterized in that it is directed against the above anti-idiotypic antibody.

The invention also relates to a fragment of the antibody according to the invention, characterized in that it may be used in place of the whole antibody. In a preferred embodiment, this antibody fragment is an F(ab')2 fragment, an Fab' fragment or an Fv fragment.

The invention also relates to a human renal carcinoma cell antigen which can be recognized by an antibody according to the invention or by one of its fragments.

Another embodiment of the invention relates to an agent for diagnosing human renal cell carcinoma, characterized in that it comprises an antibody or an antibody fragment or an antigen according to the invention as described above. According to a preferred embodiment, the diagnostic agent is characterized in that the antibody or the antibody fragment or the antigen is labeled directly or indirectly with a signal-generating label; this label is selected from radioactive isotopes and nonisotopic entities. The nonisotopic entities are selected from enzymes, dyes, haptens, luminescent agents such as radioluminescent, chemiluminescent, bioluminescent, fluorescent or phosphorescent agents, and ligands such as biotin, avidin, streptavidin or digoxigenin.

According to one embodiment, the diagnostic agent according to the invention is characterized in that the antibody, the antibody fragment or the antigen is coupled to a solid support directly or indirectly via a spacer arm. The diagnostic agent of the invention may be used in a method for diagnosing human RCCs in vitro, which comprises bringing a sample of body fluid and/or of body tissue originating from a patient in whom the presence of a cancer is suspected into contact with a diagnostic agent as described above, and determining the presence of an antigen or of an anti-idiotypic antibody or of an antibody according to the invention. The invention also relates to a diagnostic kit, characterized in that it contains the diagnostic agent described above.

The invention also relates to a composition for detecting, localizing and imaging renal cell carcinoma, comprising an antibody or an antibody fragment according to the invention; the advantages of using F(ab) or F(ab)2' antibody fragments for detecting, localizing and imaging have been described by Goldenberg D. M. (U.S. Pat. No. 4,331,647). The antibody or the antibody fragment according to the invention is labeled directly or indirectly with a signal-generating label selected from radioactive isotopes and nonisotopic entities. X-ray-emitting, gamma-ray emitting, positron-emitting and fluorescence-emitting radioisotopes are the most suitable for labeling the diagnostic agents according to the invention; radioisotopes which can be used for labeling the diagnostic agent may therefore include: Iodine$^{123}$, Iodine$^{125}$, Iodine$^{126}$, Iodine$^{131}$, Iodine$^{133}$, Bromine$^{77}$, Technetium$^{99m}$, Indium$^{111}$, Indium$^{113m}$, Gallium$^{67}$, Gallium$^{68}$, Ruthenium$^{95}$, Ruthenium$^{97}$, Ruthenium$^{103}$, Ruthenium$^{105}$, Mercury$^{207}$, Mercury$^{203}$, Rhenium$^{99m}$, Rhenium$^{101}$, Rhenium$^{105}$, Scandium$^{47}$, Tellurium$^{121m}$, Tellurium$^{122m}$, Tellurium$^{125m}$, Thulium$^{165}$, Thulium$^{167}$, Thulium$^{168}$, Copper$^{67}$, Fluorine$^{18}$, Yttrium$^{90}$, Palladium$^{100}$, Bismuth$^{217}$ and Antimony$^{211}$. There are a variety of methods known to those skilled in the art for attaching radioisotopes to the proteins either directly or via a chelating agent such as DTPA (diethylenetriaminepentaacetic acid). All these methods may be used to label the antibodies or antibody fragments of the present invention. For example, the monoclonal antibody may be labeled with Na[I$^{125}$] using the chloramine T method [Hunter W. M. and Greenwood F. C. (1962) Nature 194: 495]. The antibody or the antibody fragment may be directly labeled with Technetium$^{99m}$ using the technique of Crockford et al. (U.S. Pat. No. 4,424,200) or attached via DTPA as described by Hnatowich (U.S. Pat. No. 4,479,930). The nonisotopic entities are selected from enzymes, dyes, haptens, luminescent agents such as radioluminescent, chemiluminescent, bioluminescent, fluorescent or phosphorescent agents, and ligands such as biotin, avidin, streptavidin or digoxigenin.

The invention also relates to a method for detecting, localizing and imaging renal cell carcinoma, comprising the following steps (i) of parenteral injection, in a human, of an antibody or of an antibody fragment according to the invention, or of a composition as described above; (ii) of accumulation of the labeled antibody or of the labeled antibody fragment at the renal cell carcinoma site, after a sufficient amount of time, without the antibody or the antibody fragment binding substantially to normal cells; and (iii) of detection of the signal by means of a signal detector followed by (iv) conversion of the signal detected into an image of the renal cell carcinoma. In the context of labeling with a radioisotope, the signal detector used is preferably conventional equipment such as a gamma camera.

The invention also relates to a pharmaceutical composition intended to treat human renal carcinoma, which comprises a therapeutically effective amount of an antibody or of an antibody fragment according to the invention, and a pharmaceutically acceptable vehicle. The pharmaceutically acceptable vehicle may be any type of vehicle conventionally used in preparing injectable compositions, i.e. a diluent or a suspension agent such as an isotonic or buffered saline solution. The antibody and/or antibody fragment according to the invention may be used as a medicinal product; according to a preferred embodiment, the antibody and/or antibody fragment according to the invention is (are) used as a medicinal product for treating human renal cell carcinoma; to do this, the antibody or the antibody fragment of the pharmaceutical composition is conjugated to at least one agent selected from the group of antiproliferative, antineoplastic or cytotoxic agents. These agents are radioisotopes or nonisotopic entities.

In a preferred embodiment, the nonisotopic antiproliferative and/or antineoplastic and/or cytotoxic agent is a nucleic acid molecule. This nucleic acid molecule may be single-stranded DNA, double-stranded DNA, single-stranded RNA, double-stranded RNA or an RNA/DNA hybrid. According to a preferred embodiment, the nucleic acid molecule is double-stranded DNA or single-stranded RNA which encodes a protein product of interest which is expressed effectively in the cell. The protein products of interest are chosen from a group composed of interleukins, cytokines, lymphokines, chemokines, growth factors, killer proteins, proteins which make it possible to lift chemoresistance, and restriction enzymes; the interleukins, cytokines, lymphokines and chemokines are chosen from a group preferably composed of the interleukins Il-1, Il-2, Il-3, Il-4, Il-5, Il-6, Il-7, Il-8, Il-9, Il-10, Il-11, Il-12, Il-13, Il-14, Il-15, Il-16, Il-17 and Il-18, and the interferons α-IFN, β-IFN and γ-IFN; preferably, the protein product of interest is interleukin 2.

According to another embodiment of the invention, the nucleic acid molecule is an antisense RNA.

Conjugation of the antibody or of the antibody fragment of the present invention to an antiproliferative, antineoplastic or cytotoxic agent as described above may be used in gene therapy. According to another embodiment, conjugation of the antibody or of the antibody fragment of the present invention to an antiproliferative, antineoplastic or cytotoxic agent may be used to arrest the development of RCCs and to induce regression and/or elimination of the tumor mass.

Preferably, the antibody or the antibody fragment thus conjugated is introduced into the patient suffering from RCC and delivered to the tumor sites orally or parenterally in a pharmaceutically acceptable transporting liquid such as a physiological salt solution. Alternatively, a solution or a suspension of antibodies or of antibody fragments conjugated to an agent may be infused directly into the malignant epithelial tissue, this method preferably being used when the RCC has not metastasized.

The preferred radioisotopes conjugated to the monoclonal antibodies used for the therapy are gamma-ray-emitting radioisotopes and preferably Iodine$^{131}$, Yttrium$^{90}$, Gold$^{199}$, Palladium$^{Φ}$, Copper$^{67}$, Bismuth$^{217}$ and Antimony$^{211}$. Beta- and alpha-ray-emitting radioisotopes may also be used for the therapy. The nonisotopic entities conjugated to the monoclonal antibodies used for the therapy are multiple and varied; mention may be made of: (i) antimetabolites such as antifolate agents, methotrexate, (ii) purine and pyrimidine analogs (mercaptopurine, fluorouracil, 5-azacytidine), (iii) antibiotics, (iv) lectins (ricin, abrin) and (iv) bacterial toxins (diphtheria toxin).

The antibody or antibody fragment according to the invention is also used as a targeting agent. It thus makes it possible to target cytotoxic cells, such as human T cells, monocytes or NK cells, onto the site of the tumor, which may or may not have metastasized. The cytotoxic cells may be attached to the antibody via the Fc receptor located at the surface of these cells or via an intermediate antibody having double specificity for example; such bispecific antibodies for targeting renal cell carcinomas may be produced by fusing an immune cell producing the antibody of the present invention or the hybridoma of the present invention with a cell producing an antibody directed against the cytotoxic cell to be targeted. Bispecific antibodies may also be produced by chemically coupling two antibodies having the desired specificity. The antibody or antibody fragment according to the invention also makes it possible to target delivery vehicles for antiproliferative, antineoplastic or cytotoxic agents, onto the site of the tumor, which may or may not have metastasized. The term "delivery vehicle" is intended to denote liposomes and viral particles.

Finally, according to another preferred embodiment, the antigen or the anti-idiotypic antibody according to the invention may be used for preparing a prophylactic treatment intended to treat human carcinoma. Specifically, since the antigen or anti-idiotype antibody is specifically recognized by the antibody or the antibody fragment according to the invention, the antigen or the anti-idiotype antibody may be used for immunization in order to cause an anticancer immune response in the body.

LEGEND TO THE FIGURES

FIG. 1: Typing of RCC cell lines by indirect immunofluorescence using flow cytometry.

The cells of the ROB renal carcinoma were incubated with 5C5 conjugated to fluorescein (FITC) (A, C, E) and transferrin conjugated to Texas-red (TRIC) (B, D, F). At 4° C., 5C5 labels the cell surface (A). After 10 minutes (C, D) and 30 minutes (E, F) of internalization, 5C5 (C, E) and transferrin (D, F) are internalized and are partially codistributed in the perinuclear region where the late recycling compartment for transferrin is localized.

A renal carcinoma tumor (HIEG) was transplanted under the skin of irradiated Nude mice. The mice secondarily received, intravenously, complementary DNA encoding bacterial β-galactosidase, alone (control), or the same DNA conjugated to 5C5 via coupling involving benzoquinone. β-Galactosidase production was demonstrated by immunofluorescence labeling using a biotinylated antibody directed against β-galactosidase (Sigma laboratory), and then revealed using FITC-streptavidin (b-Gal). The nuclei of the tumor cells are visualized using DAPI and the cells are revealed by phase contrast (phase C). The β-galactosidase is detected in the tumor cells only when the mice have received the DNA conjugated to 5C5.

A renal carcinoma tumor (HIEG) was transplanted under the skin of irradiated Nude mice. The mice secondarily received, intravenously, complementary DNA encoding bacterial β-galactosidase, alone (control) or the same DNA associated with an avidin-polylysine complex (via benzoquinone) to which biotinylated 5C5 is attached (mAbAv-P1) or the same complex comprising, in addition, the biotinylated bacterial hemagglutinin toxin which makes it possible to increase the effectiveness of the gene transfer (id+Tox). β-Galactosidase production was determined by immunofluorescence labeling using a biotinylated antibody directed against β-galactosidase (Sigma laboratory), and then revealed using FITC-streptavidin (β-galactosidase). The cells are revealed by phase contrast (phase contrast). The β-galactosidase is detected in the tumor cells only when the mice have received the DNA conjugated to 5C5.

Other characteristics and advantages of the present invention will become apparent on reading the examples below.

EXAMPLES

1. Protocol for Preparing the 5C5 Hybridoma

Two Balb/C mice received an intraplantar injection of 4.5×10$^6$ cells of the BIZ human renal carcinoma provided by Dr. Jean Gogusev (Hôpital Necker-Enfants Malades [Necker Hospital for Sick Children], Paris, France) in 100 μl of 0.9% NaCl.

Eighteen days later, a booster is given with 5×10$^6$ cells of the BIZ human renal carcinoma in 50 μl of 0.9% NaCl.

Three days later, a cell suspension is prepared from the inguinal and abdominal lymph nodes of the mice.

$23 \times 10^6$ cells of the cell suspension are fused with $11.5 \times 10^6$ Sp20 Balb/C mouse myeloma cells, in the presence of PEG4000. The cell mixture is then placed into three 96-well plates filled, two days beforehand, with mouse peritoneal cells in order to select only the hybrid cells capable of developing.

A first analysis by flow cytometry on BIZ cells gave positive results for the 5C5 clone.

A second analysis made it possible to confirm this positive result. It was thus possible to freeze uncloned 5C5 vials.

A limiting dilution from a frozen vial of the 5C5 clone made it possible to obtain, after analysis by flow cytometry on BIZ cells, a 5C5 subclone. The 5C5 hybridoma could thus be frozen. The class and subclass of the 5C5 monoclonal antibody were determined using specific rabbit immunosera according to the Ouchterlony technique at the Experimental Immunology Laboratory (collaboration Professor H. BAZIN).

The 5C5 monoclonal antibody belongs to the IgG1k immunoglobulin class.

2. Characterization of the 5C5 Monoclonal Antibody:

2.1. On RCCs

Figure 1A:
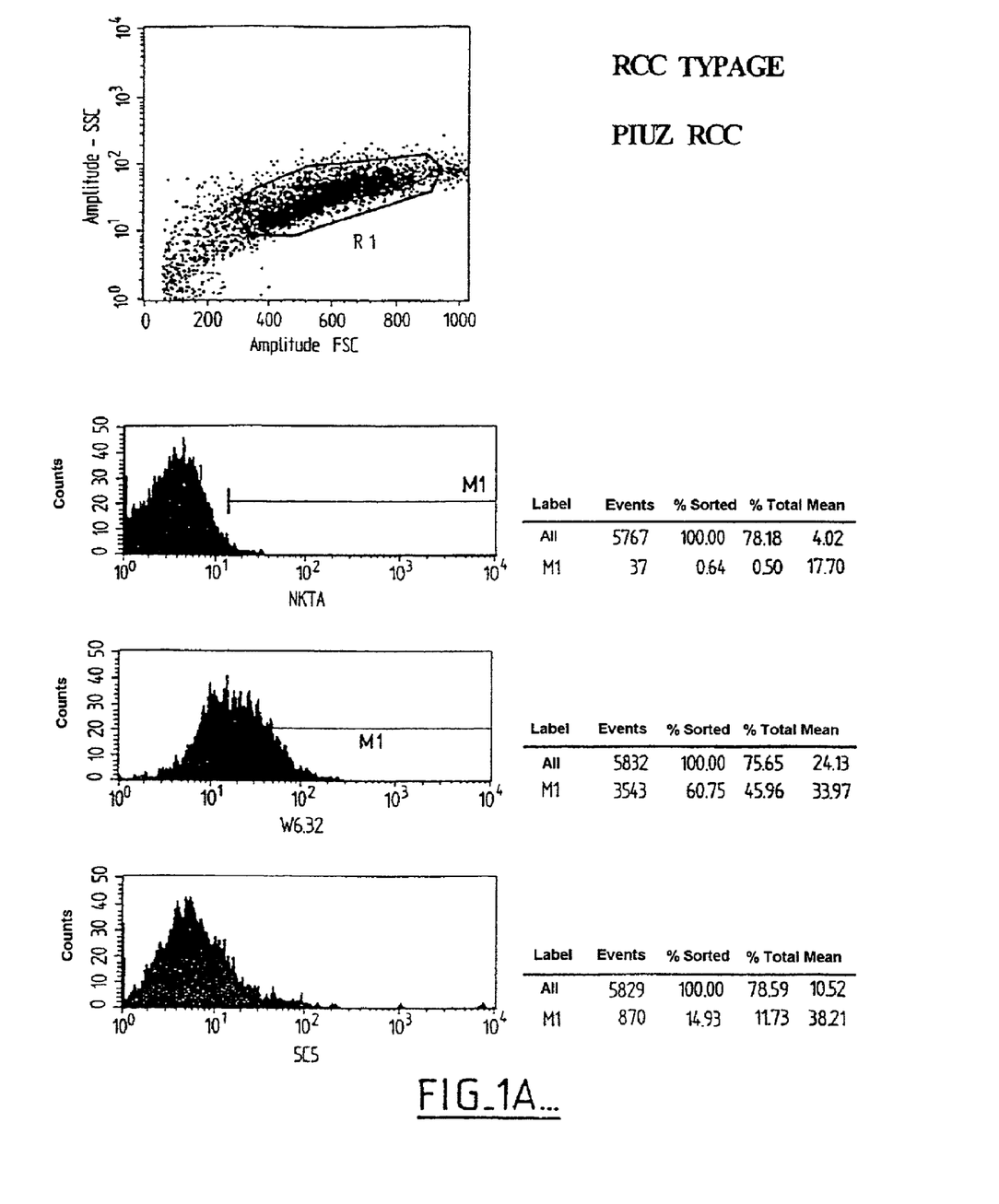
FIG. 1A: typing of the PIUZ and LAWR lines.
Figure 1B:
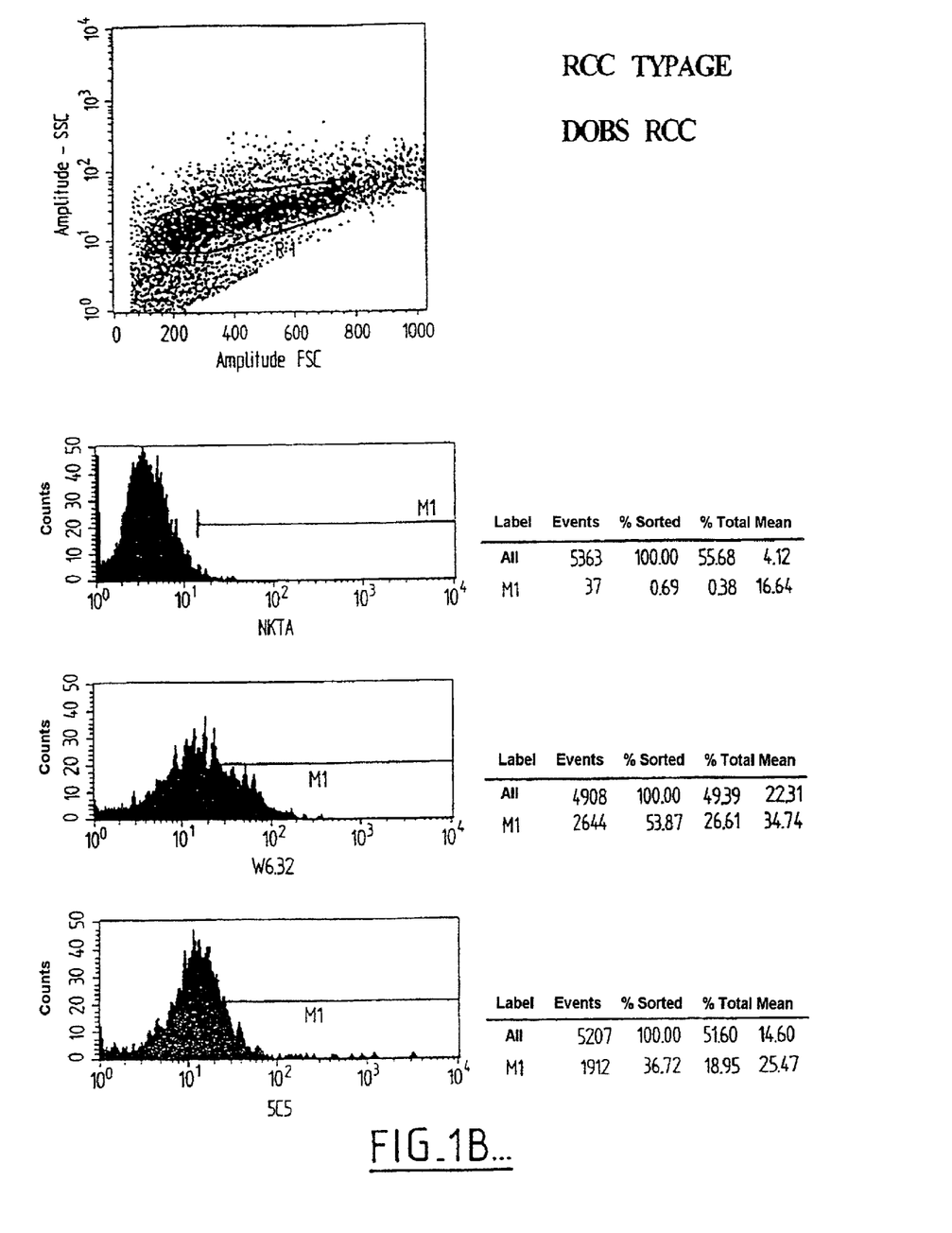
FIG. 1B: typing of the DOBS and GUIL lines.

Seventeen human RCC lines were tested by indirect immunofluorescence, by flow cytometry, using the 5C5 mAb, either from culture supernatants or from mAb immunopurified on a protein-A-Sepharose® column. The 17 human RCC lines tested are as follows: BIZ, HIEG, QUIE, BENA, PIUZ, GUIL, GUER, ROB, DURI, JOUS, GUIS, LEFR, MEGR, BLAN, DOBS, MOJ, LAWR. Only LAWR is not recognized by the 5C5 monoclonal antibody (FIG. 1).

A parallel study carried out in the presence of the G250 antibody on all of these tumors showed that the BIZ and HIEG lines did not express the G250 antibody, whereas the ROB and QUIE lines express it (results not shown).

2.2. On Other Lines The 5C5 monoclonal antibody was tested on diverse human tumor lines by direct immunofluorescence and microscopy (collaboration with Doctor J. LEPENDU, INSERM U 419, NANTES, FRANCE). The lines tested are as follows: HRT18, HLT8R, LS174T, SW48 and SW620, derived from colon tumor, LX2 derived from lung tumor, KATO derived from stomach cancer, MCF7 and ZR75, derived from breast cancer, and OVCAR derived from an ovarian tumor. All these indirect immunofluorescence experiments using the 5C5 monoclonal antibody on these human tumor lines proved to be negative (results not shown).

Figure 2:
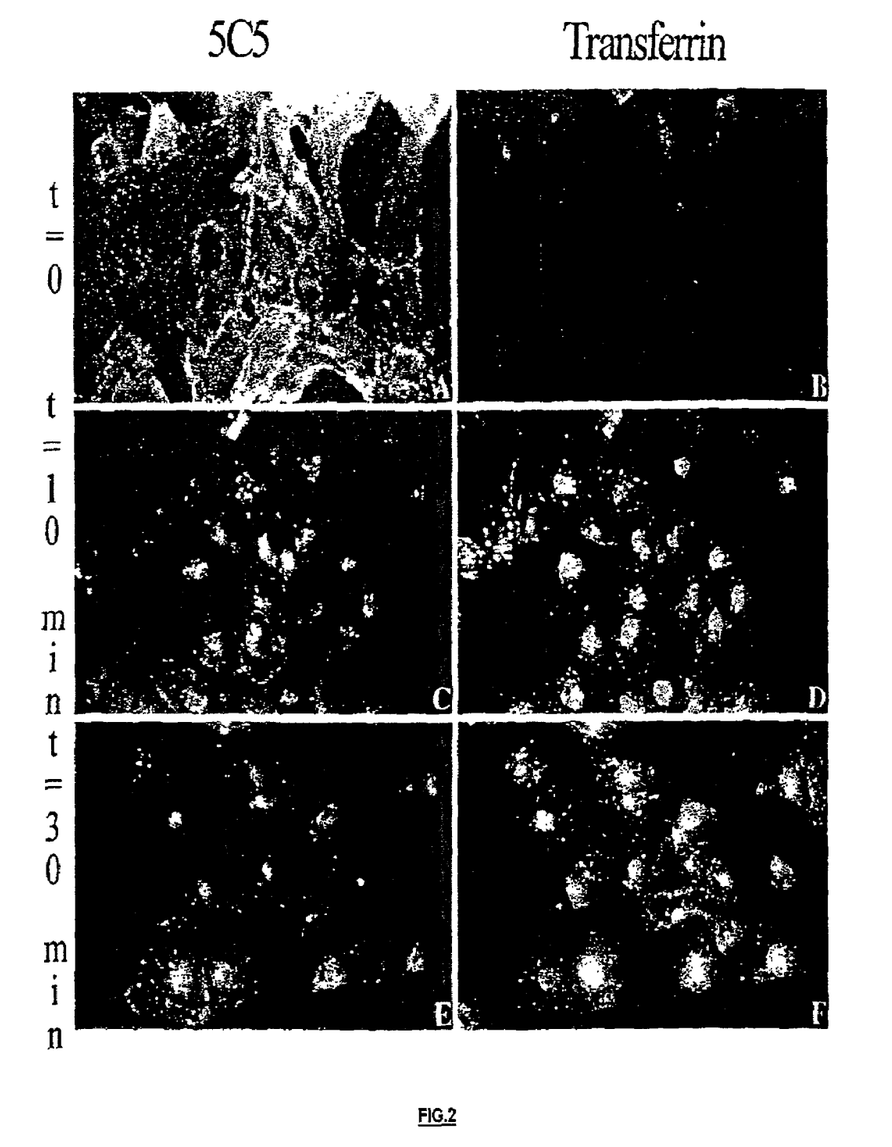
FIG. 2: Demonstration of the internalization of the 5C5 antibody in an RCC line.

3. Use of the 5C5 Monoclonal Antibody in Gene Therapy In Vitro:

The immunofluorescence experiments demonstrated that the 5C5 monoclonal antibody internalizes completely in RCCs (FIG. 2). This positive result constitutes an essential prerequisite for a vector-based approach such as antiinfection [Poncet et al. (1996) Gene Ther. 3: 731–738].

Figure 3:
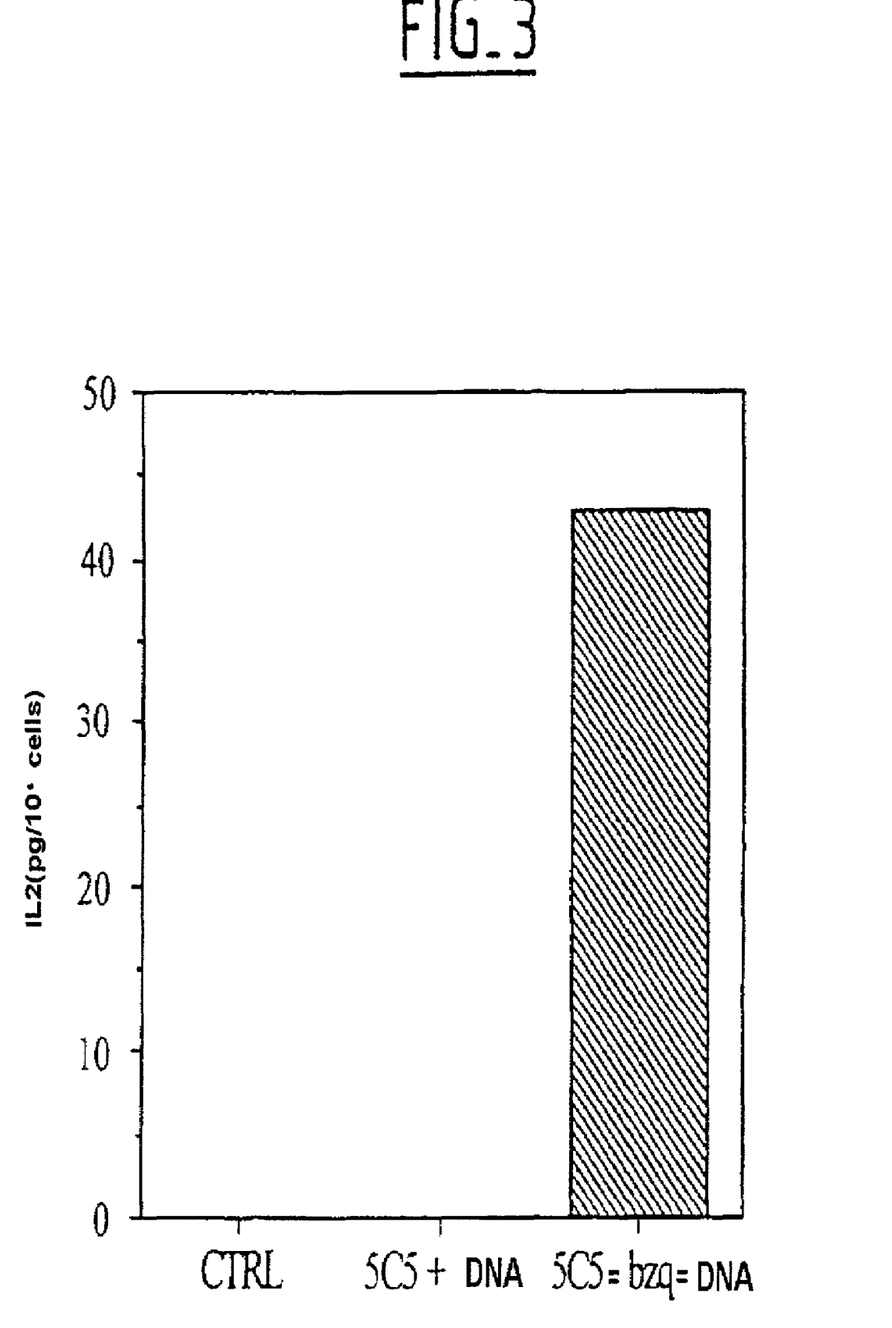
FIG. 3: Production of mouse interluekin 2 (Il-2) by ROB cells after infection.

The antiinfection experiments made it possible to demonstrate that the 5C5 monoclonal antibody is capable of vehicling a gene encoding mouse interleukin-2 (Il-2) into cells; the murine Il-2 gene thus vehicled is transcribed and expressed, as witnessed by the presence of Il-2 in the culture supernatants (FIG. 3).

4. Use of the 5C5 mAb in Genetherapy In Vivo

These experiments were carried out in collaboration with E. Angevin (I. G. R.).

4.1. 1st Experiment

Nude mice, irradiated beforehand, received a HIEG tumor transplant, positioned subcutaneously. When the tumors reach a size approximately 10×10 mm, the mice are divided into three groups:

1 naive mouse 2 mice received, via the retro-orbital intravenous route, an injection of a mixture of 10 µg of 5C5 mAb coupled to 100 µg of plasmid encoding β-galactosidase, via benzoquinone, according to the technique described previously [Poncet et al. (1996) Gene Ther. 3:731–738].

Figure 4:
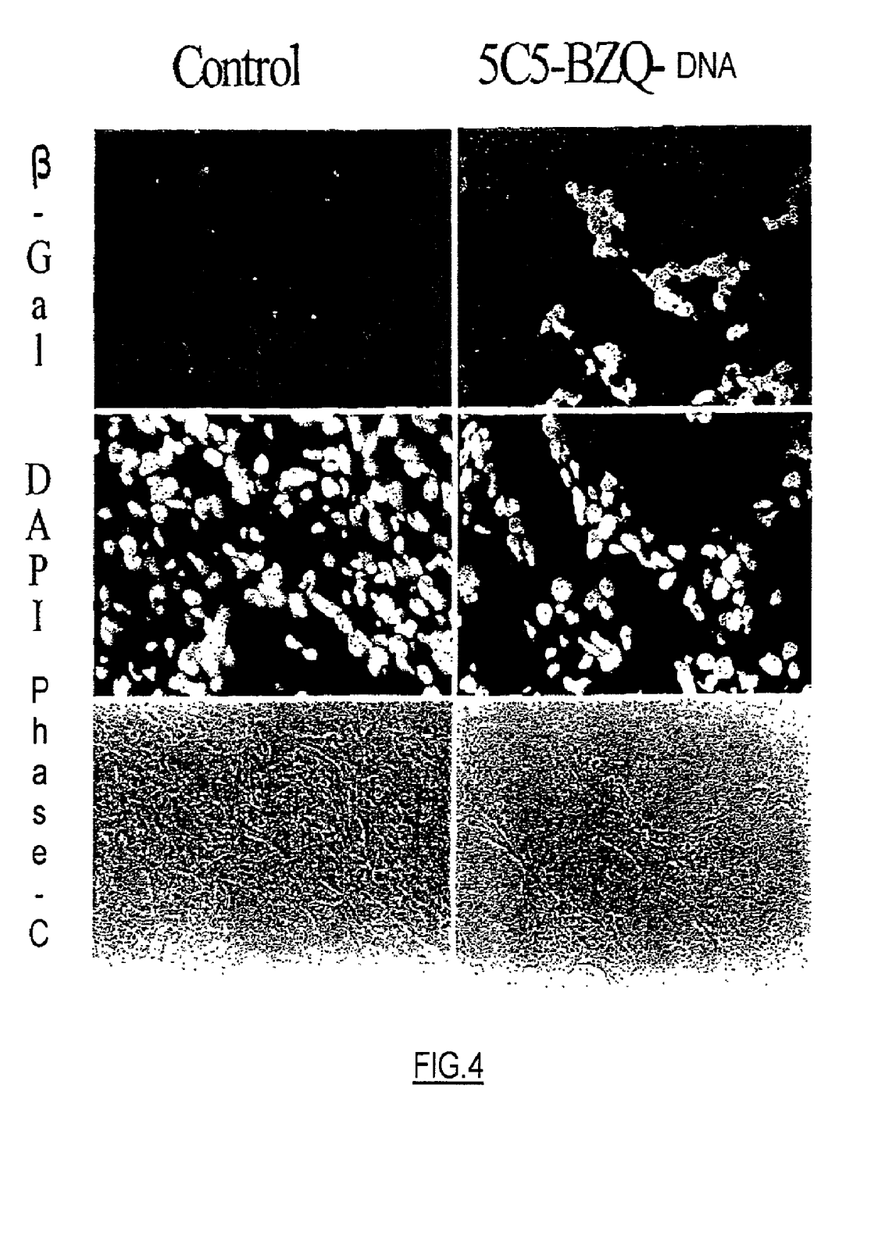
FIG. 4: Expression of β-galactosidase in RCCs in vivo, after intravenous antiinfection of a 5C5-benzoquinone-DNA conjugate.

While no enzymatic activity was found, by histochemical analysis, in the tumor of the naive mouse, 2 mice out of the 3 having received the conjugate show marked positivity (FIG. 4). A more thorough study relating to searching for enzymatic activity demonstrated, for the 2 positive mice, an absence thereof in the other organs tested, and considerable positivity in the liver of the negative mouse.

4.2. 2nd Experiment

Figure 5:
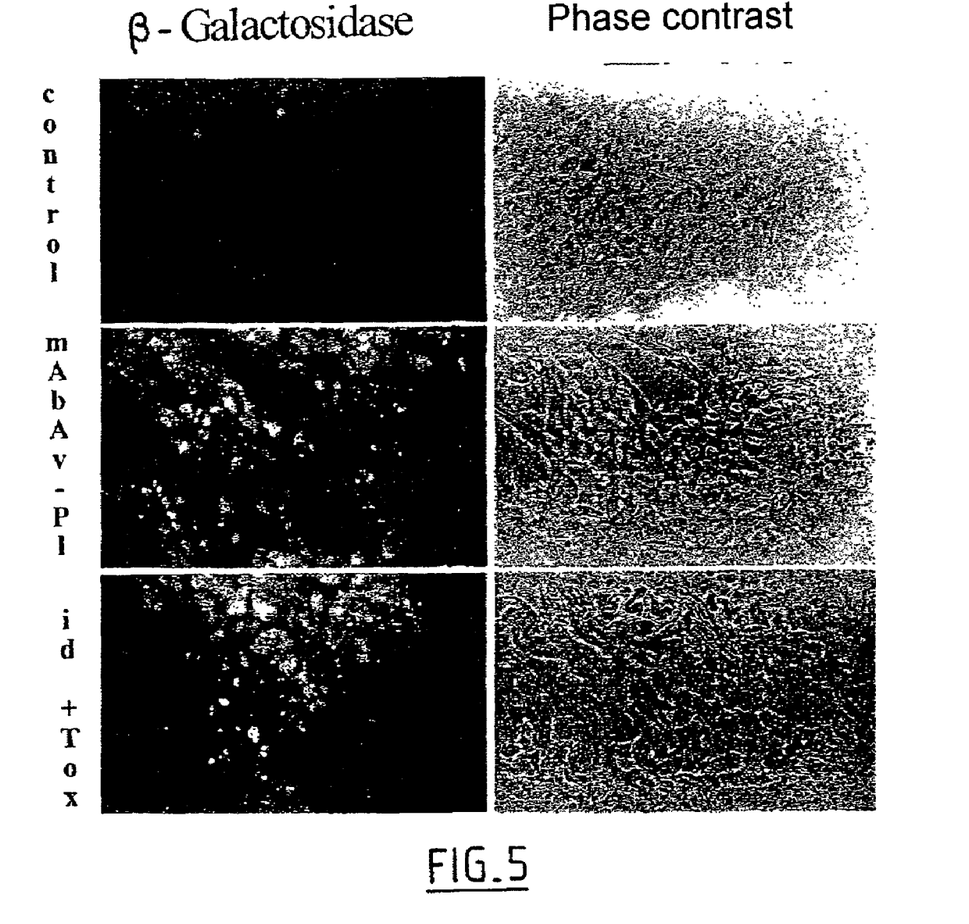
FIG. 5: Expression of β-galactosidase in RCCs in vivo, after intravenous antiinfection of a 5C5-avidin-polyLysine-toxin-DNA conjugate.

Nude mice, irradiated beforehand, received a HIEG tumor transplant, positioned subcutaneously. The 5C5 monoclonal antibody, biotinylated beforehand, is coupled to a complex which includes several components, DNA=poly-L-lysines=benzoquinone=biotin, via an avidin molecule. Finally, a biotinylated *Pseudomonas aeruginosa* exotoxin A molecule is added. Reporter activity is sought by measuring β-galactosidase expression in the tumors. Strong β-galactosidase activity was demonstrated in the group of mice having received the complete conjugate (FIG. 5).

REFERENCES

Holthafer et al. (1983) Lab. Invest. 49, 319–326.
Hunter W. M. and Greenwood F. C. (1962) Nature 194: 495.
Kaufmann O. et al. (1997) Histopathology 31:31–37.
Kinouchi T. et al. (1995) J. Urol. 154: 288–292.
Köhler and Milstein (Nature (1975) 256: 495–497.
Oberling et al. (1960) Nature 186, 402–403.
Oosterwijk E. et al. (1993) J. Clin. Oncol. 11: 738–750.
Oosterwijk E. et al. (1986) Int. J. Cancer 38: 489–494.
Poncet et al. (1996) Gene Therapy 3: 731–738.
Steffens M. G. et al. (1997) J. Clin. Oncol. 15: 1529–1537.

The invention claimed is:

1. A hybridoma denoted 5C5, as designated by the CNCM under the number I-2184.

2. A 5C5 monoclonal antibody specific for human renal carcinoma cells obtained from the hybridoma of claim 1 or an antigen binding fragment thereof.

3. The fragment as claimed in claim 2, wherein the antigen binding fragment is an F(ab')2 fragment, an Fab' fragment, or an Fv fragment.

4. An agent for diagnosing human renal cell carcinoma, wherein the agent comprises the antibody or antigen binding fragment thereof as claimed in claim 2.

5. The diagnostic agent as claimed in claim 4, wherein the antibody or antigen binding fragment thereof is labeled directly or indirectly with a signal-generating label.

6. The diagnostic agent as claimed in claim 5, wherein the label is selected from radioactive isotopes and nonisotopic entities.

7. The diagnostic agent as claimed in claim 6, wherein the nonisotopic entities are selected from the group consisting of enzymes, dyes, haptens, luminescent agents, radioluminescent agents, chemiluminescent agents, bioluminescent agents, fluorescent agents, phosphorescent agents, biotin, avidin, streptavidin, and digoxigenin.

8. The diagnostic agent as claimed in claim 4, wherein the antibody or antigen binding fragment thereof is coupled to a solid support directly or indirectly via a spacer arm.

9. A diagnostic kit, wherein the kit contains the agent as claimed in claim 4.

10. A composition for detecting, localizing, and imaging renal cell carcinoma, comprising the antibody or antigen binding fragment thereof as claimed in claim 2, such that the antibody or antigen binding fragment thereof is labeled directly or indirectly with a signal-generating label.

11. The composition as claimed in claim 10, wherein the signal-generating label is selected from radioactive isotopes and nonisotopic entities.

12. The composition as claimed in claim 11, wherein the radioactive isotopes are selected from the group consisting of Iodine$^{123}$, Iodine$^{125}$, Iodine$^{131}$, Indium$^{111}$, Ruthenium$^{97}$, Copper$^{67}$, and Technetium$^{99m}$, and wherein the nonisotopic entities are selected from the group consisting of enzymes, dyes, haptens, luminescent agents, radioluminescent agents, chemiluminescent agents, bioluminescent agents, fluorescent agents, phosphorescent agents, biotin, avidin, streptavidin, and digoxigenin.

13. A pharmaceutical composition comprising the antibody or antigen binding fragment thereof as claimed in claim 2, and a pharmaceutically acceptable vehicle.

14. The pharmaceutical composition as claimed in claim 13, wherein the antibody or antigen binding fragment thereof is conjugated to at least one radioactive agent, wherein the agent is selected from the group consisting of Iodine$^{131}$, Yttrium$^{90}$, Gold$^{199}$, Palladium$^{100}$, Copper$^{67}$, Bismuth$^{217}$, and Antimony$^{211}$.

15. A targeting agent comprising the antibody or antigen binding fragment thereof as claimed in claim 2.

16. A chimeric or humanized antibody, produced from the antibody as claimed in claim 2, or an antigen binding thereof.

17. The fragment of a chimeric or humanized antibody as claimed in claim 16, wherein the antigen binding fragment is an F(ab')2 fragment, and Fab' fragment, or an Fv fragment.

18. An agent for diagnosing human renal cell carcinoma, wherein the agent comprises the chimeric or humanized antibody or antigen binding fragment thereof as claimed in claim 16.

19. The diagnostic agent as claimed in claim 18, wherein the antibody or antigen binding fragment thereof is labeled directly or indirectly with a signal-generating label.

20. The diagnostic agent as claimed in claim 19, wherein the label is selected from radioactive isotopes and nonisotopic entities.

21. The diagnostic agent as claimed in claim 19, wherein the nonisotopic entities are selected from the group consisting of enzymes, dyes, haptens, luminescent agents, radioluminescent agents, chemiluminescent agents, bioluminescent agents, fluorescent agents, phosphorescent agents, biotin, avidin, streptavidin, and digoxigenin.

22. The diagnostic agent as claimed in claim 18, wherein the antibody or antigen binding fragment thereof is coupled to a solid support directly or indirectly via a spacer arm.

23. A diagnostic kit, wherein the kit contains the agent as claimed in claim 18.

24. A composition for detecting, localizing, and imaging renal cell carcinoma, comprising the antibody or antigen binding fragment thereof as claimed in claim 16 such that the antibody or antigen binding fragment thereof is labeled directly or indirectly with a signal-generating label.

25. The composition as claimed in claim 24, wherein the signal-generating label is selected from radioactive isotopes and nonisotopic entities.

26. The composition as claimed in claim 25, wherein the radioactive isotopes are selected from the group consisting of Iodine$^{123}$, Iodine$^{125}$, Iodine$^{131}$, Indium$^{111}$, Ruthenium$^{97}$, Copper$^{67}$, and Technetium$^{99m}$, and wherein the nonisotopic entities are selected from the group consisting of enzymes, dyes, haptens, luminescent agents, radioluminescent agents, chemiluminescent agents, bioluminescent agents, fluorescent agents, phosphorescent agents, biotin, avidin, streptavidin, and digoxigenin.

27. A pharmaceutical composition comprising the antibody or antigen binding fragment thereof as claimed in claim 16 and a pharmaceutically acceptable vehicle.

28. The pharmaceutical composition as claimed in claim 27, wherein the antibody or antigen binding fragment thereof is conjugated to at least one radioactive agent, wherein the agent is selected from the group consisting of Iodine$^{131}$, Yttrium$^{90}$, Gold$^{199}$, Palladium$^{100}$, Copper$^{67}$, Bismuth$^{217}$, and Antimony$^{211}$.

29. A targeting agent comprising the antibody or antigen binding fragment thereof, as claimed in claim 16.

30. A method for diagnosing human renal carcinoma in vitro, comprising:
   (A) bringing a sample of body fluid, or of body tissue, or of both body fluid and body tissue, originating from a patient in whom the presence of a cancer is suspected, into contact with the agent as claimed in claim 4; and
   (B) determining the presence of an antigen in the sample.

31. A method for diagnosing human renal carcinoma in vitro, comprising:
   (A) bringing a sample of body fluid, or of body tissue, or of both body fluid and body tissue, originating from a patient in whom the presence of a cancer is suspected, into contact with the agent as claimed in claim 18; and
   (B) determining the presence of an antigen in the sample.

* * * * *

UNITED STATES PATENT AND TRADEMARK OFFICE
CERTIFICATE OF CORRECTION

PATENT NO. : 7,074,613 B1
APPLICATION NO. : 09/959911
DATED : July 11, 2006
INVENTOR(S) : François Hirsch et al.

It is certified that error appears in the above-identified patent and that said Letters Patent is hereby corrected as shown below:

Title page, item (73), "Assignee: Centre National de la Rechershe Scientifique" should read --Assignee: Centre National de la Recherche Scientifique--.

Signed and Sealed this

Third Day of October, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,074,613 B1 | Page 1 of 1 |
| APPLICATION NO. | : 09/959911 | |
| DATED | : July 11, 2006 | |
| INVENTOR(S) | : Francois Hirsch and Eric Angevin | |

It is certified that error appears in the above-identified patent and that said Letters Patent is hereby corrected as shown below:

Col. 9, Line 50 Claim 21 should read:

--21. The diagnostic agent as claimed in claim 20, wherein the nonisotopic entities are selected from the group consisting of enzymes, dyes, haptens, luminescent agents, ra dioluminescent agents, chemiluminescent agents, bioluminescent agents, fluorescent agents, phosphorescent agents, biotin, avidin, streptavidin, and digoxigenin.--

Signed and Sealed this

Fifth Day of December, 2006

JON W. DUDAS
*Director of the United States Patent and Trademark Office*